United States Patent [19]

Sakai

[11] Patent Number: 4,743,343

[45] Date of Patent: May 10, 1988

[54] METHOD OF REGENERATING ALCOHOL-BASED ANTIFREEZING LIQUID

[76] Inventor: Tadaaki Sakai, 39-8 Yamadanishi 3-chome, Suita-shi, Osaka, Japan

[21] Appl. No.: 948,331

[22] Filed: Dec. 31, 1986

[51] Int. Cl.$^4$ .......................... B01D 3/02; C07C 29/80
[52] U.S. Cl. ........................................ 203/22; 203/18;
 203/19; 203/40; 203/49; 203/87; 203/DIG. 19;
 62/64; 202/175; 202/180; 202/186; 202/197;
 202/198; 426/524; 568/916
[58] Field of Search ...................... 203/18, 19, 49, 87,
 203/22, 71, 40, DIG. 13, DIG. 19, 99, DIG. 11;
 202/180, 234, 233, 235, 175, 186, 198; 159/16.1,
 47.1; 62/64, 62; 426/524; 568/916

[56] References Cited

U.S. PATENT DOCUMENTS

| | | | |
|---|---|---|---|
| 1,490,520 | 4/1924 | Steffens | 203/19 |
| 1,833,717 | 11/1931 | Laird | 203/19 |
| 3,361,649 | 1/1968 | Karter | 202/197 |
| 4,303,478 | 12/1981 | Field | 203/19 |
| 4,305,790 | 12/1981 | Kramer | 203/19 |
| 4,327,184 | 4/1982 | Johnson et al. | 203/87 |
| 4,344,828 | 8/1982 | Melton | 203/19 |
| 4,347,321 | 8/1982 | Lionelle et al. | 203/87 |
| 4,601,909 | 7/1986 | Nagoshi | 426/524 |

*Primary Examiner*—Wilbur Bascomb
*Attorney, Agent, or Firm*—Koda and Androlia

[57] ABSTRACT

This invention relates to a method of regenerating an alcohol-based antifreezing liquid, and more particularly to a method of concentrating and regenerating an alcohol-based antifreezing liquid diluted through water absorption by removing water therefrom.

The antifreezing liquid containing water is introduced into an evaporation vessel. The liquid is then heated to a temperature at which components other than alcohol of the liquid are unlikely to be affected in their properties while air is fed thereinto. Thus alcohol and water vapors are generated. These vapors are first cooled to a temperature at which only water is condensed. After water is removed, cooling is effected at a lower temperature. At this stage, the alcohol vapor is condensed, and thus concentrated alcohol, almost water-free, is collected.

The alcohol thus collected and nonfreezing and high boiling-point components other than alcohol in the evaporation vessel are again mixed into a concentrated antifreezing liquid.

7 Claims, 1 Drawing Sheet

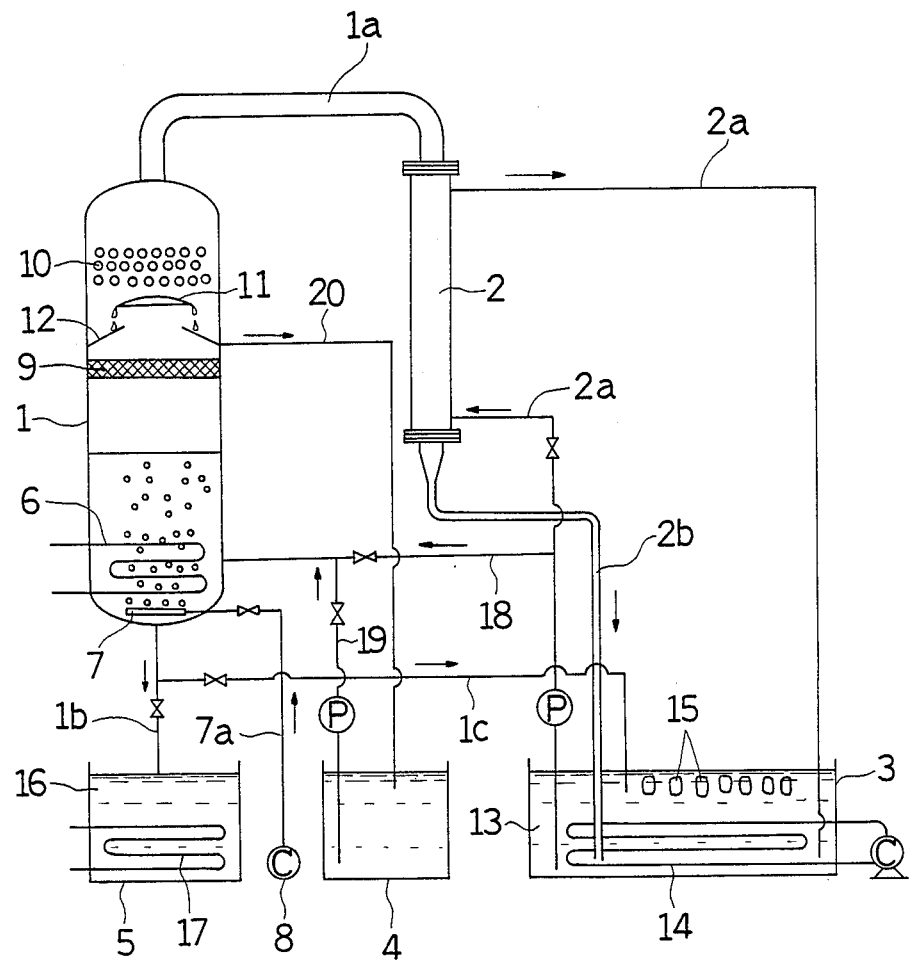

METHOD OF REGENERATING ALCOHOL-BASED ANTIFREEZING LIQUID

BACKGROUND OF THE INVENTION

1. Field of the Invention

This invention relates to a method of regenerating an alcohol-based antifreezing liquid and, more specifically, to a method of regenerating an alcohol-based antifreezing liquid diluted through water absorption by concentrating the liquid through removal of water therefrom.

2. Prior Art

Various kinds of alcohol-based antifreezing liquids have been known which include, for example, ethanol and other alcohols, and mixtures of alcohol and other liquids, such as propylene glycol. Such alcohol-based antifreezing liquid is generally utilized in freezing foodstuffs, and for this purpose the so-called liquid immersion method is often used. This method is such that foodstuffs are immersed for a given period of time in an alcohol-based antifreezing liquid which has been stored and cooled in a tank open on the top side, being then removed.

In the liquid immersion method, the antifreezing liquid is cooled to several tens of degree below zero centigrade or even to a temperature near $-100°$ C., and in such condition the surface of the antifreezing liquid is in contact with air. Therefore, moisture in the water is absorbed through the liquid surface into the liquid and the antifreezing liquid is thus diluted. When a low-temperature antifreezing liquid is diluted with water, some poor condition of agitation develops and this results in a liquid temperature rise. In order to prevent such temperature rise, a usual practice has been to discharge the antifreezing liquid in part from the tank periodically and add a fresh supply of antifreezing liquid (of high concentration). However, the trouble is that such practice involves high running cost and does not pay. Moreover, such practice poses a problem from the standpoint of waste treatment or disposal.

SUMMARY OF THE INVENTION

This invention is intended to overcome such difficulty of the conventional practice. Accordingly, it is a primary object of the invention to provide a method for reutilization of an alcohol-based antifreezing liquid diluted through absorption of moisture or water from the air by removing water from the liquid.

It is another object of the invention to a method for such reutilization which can be carried out at low cost and by employing an apparatus which is simple in construction and inexpensive to manufacture.

It is a further object of the invention to provide a method for such reutilization which permits accurate and prompt removal of water only without detriment to the ingredients of the antifreezing liquid.

In order to accomplish aforesaid objects, according to this invention, an alcohol-based antifreezing liquid having a water content is introduced into an evaporation vessel, in which the liquid is heated under feed of air to such extent as will cause no change to ingredients of the liquid other than alcohol, whereby alcohol and water vapors are generated. Then, the vapors are cooled to such temperature as will allow the water vapor to be condensed and not the alcohol vapor. The resulting water through condensation is discharged from the evaporation vessel, whereas the remaining vapor, that is, alcohol vapor, is introduced into a condenser, in which the vapor is cooled to a lower temperature to allow it to be condensed. This invention utilizes the difference in dew point between water vapor and alcohol vapor in separating and collecting alcohol. In order to prevent any change in the properties of ingredients other than alcohol of the alcohol-based antifreezing liquid and from the standpoint of energy saving or running cost reduction, the liquid introduced into the evaporation vessel is heated to temperatures of $40°-100°$ C. and not to a very high temperature. Evaporation should be effected quickly in order to prevent property change in said other ingredients. From this view point, heating to a higher temperature is desirable, but this point can be compensated by air agitation as described hereinafter. Anyhow, for the above stated reason, aforesaid temperatures are used.

Since the heating temperature is rather low, vapor developed is mostly of alcohol and water, but it may include to a small degree vapor of such ingredients as, for example, propylene glycol. The vapor is then cooled to a temperature at which water vapor only is condensed. At this stage, the water vapor is condensed and the resulting water is discharged from the evaporation vessel. The dew point of the alcohol vapor is lower than that of the water vapor, the alcohol vapor is not condensed at this stage. Since the water vapor is removed, the alcohol concentration of the remaining vapor is very high at this stage. The vapor containing a large amount of alcohol vapor is then cooled to a temperature lower than the previous cooling temperature and is thus condensed. Therefore, the liquid leaving the condenser is almost all alcohol. In this way, it is possible to remove water from the antifreezing liquid, and thereby to concentrate and regenerate the liquid.

The water which had been contained in the antifreezing liquid is discharged from the evaporation vessel as above mentioned, but not all water content is evaporated and some water may remain in the evaporation vessel. Other components, such as propylene glycol, almost all remain in the evaporation vessel because of their higher boiling point. Therefore, the liquid remaining in the evaporation vessel, if its water content is small, may be reutilized by being mixed with the condensed liquid containing a large amount of alcohol. Even an antifreezing liquid consisting of a mixture liquid can be reused by removing water in this way, without change in its component ratio. If the amount of its water content is relatively large, it is desirable that the liquid is first stored in a storage tank and is heated to remove water before it is reutilized.

According to this invention, when the antifreezing liquid in the evaporation vessel is heated, air is supplied into the vessel, so that it is possible to equalize the temperature of the liquid by stirring and to increase the area of contact with air through bubbles in the liquid, thereby to provide increased evaporation area. Evaporation of the antifreezing liquid can thus be facilitated. Further, mist-like droplets develop under said air feed and this further facilitates alcohol evaporation. In addition, upward air streams are produced within the evaporation vessel by said air feed and therefore the vapor developed is quickly discharged from the evaporator vessel. In this respect, too, said air serves to facilitate the generation of vapor. Since vaporization is easily and promptly effected in this way, heating temperatures can be set rather low. This is helpful in preventing the decomposition and change in properties of components other than alcohol.

According to an advantageous development of this invention, a mist catcher for collecting mists of antifreezing liquid in the evaporator vessel is provided. By this arrangement it is possible to prevent mists of antifreezing liquid from reaching the condenser. Therefore, the alcohol concentration of the condensed liquid may be further improved.

According to another advantageous development of the invention, it is possible to cool the condenser with the alcohol-based antifreezing liquid to be regenerated. This provides an advantage that no refrigerant is required for condenser cooling.

BRIEF DESCRIPTION OF THE DRAWING

The single FIGURE is a schematic representation of an apparatus for carrying ou the method of the invention.

DETAILED DESCRIPTION OF THE INVENTION

One preferred mode for carrying out the method of the invention will now be described with reference to the drawing.

In the drawing, numeral 1 designates an evaporator vessel, 2 designates a condenser, 3 designates a freezing tank, and 4 designates a washing tank. In the evaporator 1 there are provided a heater 6 for heating the antifreezing liquid and an air feeder 7 at the bottom. The air feeder 7 is connected to an external compressor 8 through piping 7a and is designed to blow out air from a multiplicity of fine holes provided on the surface. A mist catcher 9 is provided generally centrally in the evaporator vessel 1. This catcher 9 is intended to prevent liquid mists from moving upward in the vessel 1 to reach a heat exchanger 10. The mist catcher 9 may be made of a plurality of metal wire nets, one laid on top of another. In the upper portion of the evaporator vessel 1 there is disposed a heat exchanger 10 above the mist catcher 9, and a baffle plate 11 and a guide plate 12 between the heat exchanger 10 and the mist catcher 9. The buffle plate 11 serves chiefly to change the direction of vapor streams flowing upward in the evaporator vessel 1 and concurrently to let water droplets onto the guide plate 11 as they are cooled and condensed by the heat exchanger 10. Water collected on the guide plate 11 is discharged out of the evaporation vessel 1. Vapor produced in the evaporation vessel 1 is guided to the condenser 2 through a duct 1a as it flows outward from the top of the vessel 1.

The condenser 2 performs condensation of vapor through heat exchange utilizing the alcohol-based antifreezing liquid 13 stored in the freezing tank 3. The antifreezing liquid 13 is allowed to circulate by passing through the condenser 2 via piping 2a. The liquid condensed in the condenser 2 (which is almost entirely alcohol) is fed to the freezing tank 3 through a duct 2b.

The freezing tank 3 stores therein alchol-based antifreezing liquid 13 and is cooled by a refrigerant flowing through a cooling pipe 14. Cooling temperature is generally set at a suitable temperature within the range of $-20°$ to $-80°$ C. In the liquid immersion method, to-be-frozen items 15, such as meats, sea food, and processed foodstuffs, are frozen by being immersed for a given period of time.

The washing tank 4 contains water therein. It is employed for washing frozen items 15 to remove a deposit of antifreezing liquid thereon. Therefore, if washing is carried out in large quantities, considerable amount of antifreezing liquid will remain in the washing tank 4.

The storage tank 5 is for storing the liquid collected from the bottom of the evaporation vessel 1 after the completion of an evaporation cycle. A heater 17 is disposed in the tank 5. The liquid 16 is composed mostly of components other than alcohol of the antifreezing liquid, which components have a high boiling point and may contain a slight amount of water. The heater 17 is employed in removing any water contained in the liquid by heating the liquid. If a single kind of alcohol, e.g., ethanol, is used as an antifreezing liquid, the liquid 16 is water only, but where a mixture liquid consisting of 50 wt % of ethanol and 50 wt % of propylene glycol is used as an antifreezing liquid, the liquid 16 will include water and propylene glycol.

The method of the invention for regenerating an alcohol-based antifreezing liquid by removing water as an impurity, by employing the above described apparatus, will be further explained.

The antifreezing liquid containing water in the freezing tank 3 is first transported to the evaporation vessel 1 through piping 18. The piping 18 is connected to the piping 2a which leads to the condenser 2. Accordingly, the antifreezing liquid 13 is supplied to the condenser 2 concurrently when it is fed to the evaporator vessel 1. If the water in the washing tank 4 contains a large amount of antifreezing liquid, it is possible to transport this water also to the evaporator vessel 1 through piping 19. It is noted that this method is carried out on a batch operation basis; therefore, a predetermined quantity of antifreezing liquid is fed to the evaporation vessel 1 for regeneration each time.

The antifreezing liquid supplied to the evaporator vessel 1 is heated by the heater 6 to a temperature of the order of 40° to 100° C. while air is released from the air feeder 7, and by this heating the alcohol and water are evaporated. Such heating under air agitation does not only facilitate evaporation of both alcohol and water, but also causes mists of the liquid to spread in the space above the surface of the antifreezing liquid. Therefore, evaporation of alcohol and water can be effectively performed even in an gaseous phase. During this process, components of the liquid other than alcohol, for example, propylene glycol, if the liquid is a mixture of alcohol and propylene glycol, will mostly remain in the evaporation vessel 1, because propylene glycol has a high boiling point and is unlikely to evaporate at a temperature within above said range. Further, because of the low temperature heating, the other component of the liquid, such as propylene glycol or the like, is not subject to any deterioration in its properties under such heating. A critical temperature at which propylene glycol is subject to qualitative change is about 180° C., and heating is carried out at a much lower temperature.

Both the alcohol vapor and the water vapor developed in the evaporation vessel 1 flow upward in the vessel 1 and after passing through the mist catcher 9 they are guided to the heat exchanger 10 passing through the space between the baffle plate 11 and the guide plate 12. Mists of the antifreezing liquid are collected by the mist catcher 9, and therefore they are never allowed to reach the heat exchanger 10. Cooling water of about 3° to 27° C. is flowing through the heat exchanger 10. Accordingly, water vapor only is condensed. Water droplets thus developed are allowed to drop directly or via the baffle plate 11 on the guide plate 12 for collection and are then delivered to the washing tank 4 through piping 20 for reutilization. The vapor from which mists and water vapor have thus been removed have a high concentration of alcohol. The vapor is delivered to the condenser 2 passing through the duct 1a from the top of the vessel and is condensed therein. The resulting alcohol liquid is delivered through the duct 2b to the freezing tank 3.

According to this invention, air is blown out into the evaporation vessel 1 so that upward flowing air streams are present in the vessel 1. Therefore, vapor developed is allowed to travel upward quickly. Simultaneously, a part of the vapor can be delivered to the condenser. Therefore, the vapor in the vessel 1 is discharged promptly. In this respect, too, the air feeder 7 has a function of facilitating the evaporation of the antifreezing liquid.

After completion of evaporation cycle, the liquid remaining in the evaporation vessel 1 can be discharged into the storage tank 5 through the piping 1b. Generally, some water residue is present in this liquid 16, and therefore the liquid 16 is heated to 40°-120° C. by the heater 17 to evaporate the water. Thus, all components of the antifreezing liquid other than alcohol can be collected.

Where a mixture liquid is used as an antifreezing liquid, alcohol is condensed and automatically returned to the freezing tank 3, but other components remain in the evaporation vessel 1. Therefore, if such condition is kept as it is, the component ratio of the antifreezing liquid in the freezing tank 3 cannot be constant. Accordingly, it is necessary to measure such ratio periodically to check for the necessity of making up for any deficiency. For such replenishment, the liquid 16 in the storage tank 5 can be utilized. For this purpose, in conjunction with the piping 1b for the evaporator 1 there is provided a branch piping 1c which leads to the freezing tank 3. By using the piping 1b, therefore, it is possible to transport the liquid 16 from the evaporator vessel 1 directly to the freezing vessel 3.

The individual pipings in the apparatus are provided with valves so that wherever necessary the valves are operated for open-close control of flow channels. For example, the valve for the piping 1b is closed and the valve for the piping 1c is opened to permit the liquid 16 in the evaporation vessel 1 to the delivered directly to the freezing tank 3.

What is claimed is:

1. A method of regenerating an alcohol-based antifreezing liquid comprising the step of introducing a alcohol-based antifreezing liquid containing water into an evaporator vessel, heating the liquid to such a temperature as will not cause any change in the properties of components of the liquid other than alcohol while feeding air into the liquid, thereby generating alcohol vapor and water vapor, the step of cooling the vapors to a temperature at which the alcohol vapor is not subject to condensation, whereas the water vapor is subject to condensation, and discharging the resulting water from the evaporation vessel, and the step of introducing the vapor from which the water vapor has been removed by condensation into a condenser and cooling the vapor to a lower temperature, thereby condensing the alcohol vapor.

2. A method as set forth in claim 1, wherein the step of generating vapor is carried out while mists of antifreezing liquid which are generated within the evaporation vessel are collected by means of a mist catcher.

3. A method as set forth in claim 1, wherein cooling of the condenser is carried out by using the alcohol-based antifreezing liquid t be regenerated.

4. A method as set forth in claim 1, wherein the heating temperature for the antifreezing liquid is 40°-100° C.

5. A method as set forth in claim 1 or 4, wherein the first cooling of the vapor generated is carried out in a temperature range of 3°-27° C.

6. A method as set forth in claim 2, wherein the mist catcher catches said mists successively on a plurality of metal wire nets, one placed over another.

7. A method as set forth in claim 1, wherein the supply of air into the antifreezing liquid in the evaporator vessel is carried out by supplying compressed air to an air feeder disposed in the evaporator vessel.

* * * * *